(12) United States Patent
Shi et al.

(10) Patent No.: US 11,041,160 B2
(45) Date of Patent: Jun. 22, 2021

(54) INDUSTRIAL KERATINASE VIA GENETIC ENGINEERING AND USE THEREOF

(71) Applicant: JIANGNAN UNIVERSITY, Wuxi (CN)

(72) Inventors: Jinsong Shi, Wuxi (CN); Zhenghong Xu, Wuxi (CN); Jinsong Gong, Wuxi (CN); Heng Li, Wuxi (CN); Chang Su, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 151 days.

(21) Appl. No.: 16/343,630

(22) PCT Filed: Jun. 1, 2018

(86) PCT No.: PCT/CN2018/089618
§ 371 (c)(1),
(2) Date: Apr. 19, 2019

(87) PCT Pub. No.: WO2019/085468
PCT Pub. Date: May 9, 2019

(65) Prior Publication Data
US 2020/0385745 A1     Dec. 10, 2020

(30) Foreign Application Priority Data
Nov. 1, 2017   (CN) .......................... 201711058163.5

(51) Int. Cl.
C12N 15/77    (2006.01)
C12N 9/64     (2006.01)
C12R 1/13     (2006.01)

(52) U.S. Cl.
CPC ........... *C12N 15/77* (2013.01); *C12N 9/6424* (2013.01); *C12R 1/13* (2013.01)

(58) Field of Classification Search
None
See application file for complete search history.

(56) References Cited

FOREIGN PATENT DOCUMENTS

| CN | 102936588 A | 2/2013 |
|---|---|---|
| CN | 106282210 A | 1/2017 |
| CN | 107828765 A | 3/2018 |

OTHER PUBLICATIONS

Zhang et al., "Biochemical characterization of a novel surfactant-stable serine keratinase with no collagenase activity from Brevibacillus parabrevis CGMCC 10798", International Journal of Biological Macromolecules, 2016, vol. 93, pp. 843-851.*
GenBank Accession No. WP_080967144.1 (Apr. 9, 2017).

* cited by examiner

*Primary Examiner* — Suzanne M Noakes
(74) *Attorney, Agent, or Firm* — SZDC Law P.C.

(57) ABSTRACT

The invention relates to the technical field of industrial biotechnologies, and discloses a keratinase mutant with improved thermal stability and use thereof. The asparagine at position 181, the tyrosine at position 217, and the serine at position 236 in the keratinase derived from *Brevibacillus parabrevis* (CGMCC No. 10798) are engineered by site-direction mutation, and combined at random to obtain an enzyme with combined mutations. The invention realizes the remarkable improvement of the thermal stability of keratinase, and has good theoretical value and application prospect.

13 Claims, 4 Drawing Sheets

Specification includes a Sequence Listing.

SEQUENCE LISTING

<160> NUMBER OF SEQ ID NOS: 14

<210> SEQ ID NO 1
<211> LENGTH: 275
<212> TYPE: PRT
<213> ORGANISM: Artificial sequence
<220> FEATURE:
<223> OTHER INFORMATION: Asn at position 181 of the WT keratinase
      mutated into Asp

<400> SEQUENCE: 1

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Tyr Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Ser Gly Ser Thr Ala Leu Lys Asn Thr Val Asp Thr Ala Asn Asn
    130                 135                 140

Arg Gly Val Val Val Val Ala Ala Ala Gly Asn Ser Gly Ser Ser Gly
145                 150                 155                 160

Ser Ser Ser Thr Val Gly Tyr Pro Ala Lys Tyr Asp Ser Thr Ile Ala
                165                 170                 175

Val Ala Asn Val Asp Ser Asn Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
        275

<210> SEQ ID NO 2
<211> LENGTH: 275
<212> TYPE: PRT
<213> ORGANISM: Artificial sequence
<220> FEATURE:
<223> OTHER INFORMATION: Tyr at position 218 mutated into Ser

<400> SEQUENCE: 2

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65              70                  75                  80

Val Leu Gly Val Ala Pro Ser Ala Ser Leu Tyr Ala Val Lys Val Leu
                85                  90                  95

Asp Arg Tyr Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Thr Val Asp Thr Ala Asn Asn
    130                 135                 140

Arg Gly Val Val Val Ala Ala Gly Asn Ser Gly Ser Ser Gly
145                 150                 155                 160

Ser Ser Ser Thr Val Gly Tyr Pro Ala Lys Tyr Asp Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Ser Thr Gly Thr Ser Met Ala Ser
    210                 215                 220

Pro His Val Ala Gly Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
            245                 250                 255

Leu Gly Asp Ser Phe Tyr Tyr Gly Lys Gly Leu Ile Asn Val Gln Ala
        260                 265                 270

Ala Ser Asn
        275

<210> SEQ ID NO 3
<211> LENGTH: 275
<212> TYPE: PRT
<213> ORGANISM: Artificial sequence
<220> FEATURE:
<223> OTHER INFORMATION: Ser at position mutated into Cys

<400> SEQUENCE: 3

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

```
Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Tyr Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Thr Val Asp Thr Ala Asn Asn
    130                 135                 140

Arg Gly Val Val Val Ala Ala Gly Asn Ser Gly Ser Ser Gly
145                 150                 155                 160

Ser Ser Ser Thr Val Gly Tyr Pro Ala Lys Tyr Asp Ser Thr Ile Ala
                165                 170                 175

Val Ala Asn Val Asn Ser Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
210                 215                 220

Pro His Val Ala Gly Ala Ala Leu Ile Leu Cys Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
    275

<210> SEQ ID NO 4
<211> LENGTH: 275
<212> TYPE: PRT
<213> ORGANISM: Artificial sequence
<220> FEATURE:
<223> OTHER INFORMATION: parent protease

<400> SEQUENCE: 4

Ala Gln Thr Val Pro Tyr Gly Ile Pro Gln Ile Lys Ala Pro Ala Val
 1               5                  10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
     50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Tyr Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Thr Val Asp Thr Ala Asn Asn
    130                 135                 140
```

Arg Gly Val Val Val Ala Ala Ala Gly Asn Ser Gly Ser Ser Gly
145                 150                 155                 160

Ser Ser Ser Thr Val Gly Tyr Pro Ala Lys Tyr Asp Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
        275

<210> SEQ ID NO 5
<211> LENGTH: 22
<212> TYPE: DNA
<213> ORGANISM: Artificial sequence
<220> FEATURE:
<223> OTHER INFORMATION: primer

<400> SEQUENCE: 5
ttgccaatgt agatagtaac aa                                            22

<210> SEQ ID NO 6
<211> LENGTH: 24
<212> TYPE: DNA
<213> ORGANISM: Artificial sequence
<220> FEATURE:
<223> OTHER INFORMATION: primer

<400> SEQUENCE: 6
tgacattgtt actatctaca ttgg                                          24

<210> SEQ ID NO 7
<211> LENGTH: 24
<212> TYPE: DNA
<213> ORGANISM: Artificial sequence
<220> FEATURE:
<223> OTHER INFORMATION: primer

<400> SEQUENCE: 7
ggatacactt cttatagcgg aaca                                          24

<210> SEQ ID NO 8
<211> LENGTH: 24
<212> TYPE: DNA
<213> ORGANISM: Artificial sequence
<220> FEATURE:
<223> OTHER INFORMATION: primer

<400> SEQUENCE: 8
ccatagatgt tccgctataa gaag                                          24

<210> SEQ ID NO 9
<211> LENGTH: 24
<212> TYPE: DNA

```
<213> ORGANISM: Artificial sequence
<220> FEATURE:
<223> OTHER INFORMATION: primer

<400> SEQUENCE: 9
cagcgcttat tctttgcaaa aacc                                          24

<210> SEQ ID NO 10
<211> LENGTH: 23
<212> TYPE: DNA
<213> ORGANISM: Artificial sequence
<220> FEATURE:
<223> OTHER INFORMATION: primer

<400> SEQUENCE: 10
ttcgggtttt tgcaaagaat aag                                           23

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
ttgccaatgt agatagtaac aa                                            22

<210> SEQ ID NO 12
<211> LENGTH: 24
<212> TYPE: DNA
<213> ORGANISM: Artificial sequence
<220> FEATURE:
<223> OTHER INFORMATION: primer

<400> SEQUENCE: 12
tgacattgtt actatctaca ttgg                                          24

<210> SEQ ID NO 13
<211> LENGTH: 24
<212> TYPE: DNA
<213> ORGANISM: Artificial sequence
<220> FEATURE:
<223> OTHER INFORMATION: primer

<400> SEQUENCE: 13
cagcgcttat tctttgcaaa aacc                                          24

<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
ttcgggtttt tgcaaagaat aag                                           23
```

INDUSTRIAL KERATINASE VIA GENETIC ENGINEERING AND USE THEREOF

This application is the National Stage Application of PCT/CN2018/089618, filed on Jun. 1, 2018, which claims priority to Chinese Patent Application No.: 201711058163.5, filed on Nov. 1, 2017, which is incorporated by reference for all purposes as if fully set forth herein.

FIELD OF THE INVENTION

The invention relates to the technical field of industrial biotechnologies and more particularly to a keratinase mutant with improved thermal stability and use thereof.

DESCRIPTION OF THE RELATED ART

Keratin is an insoluble protein that is difficult to be degraded and widely distributed in nature, and is the third largest class of polymers following cellulose and chitosan. It is rich in the skin, hair, feathers, horns, nails, and beaks of the vertebrates and in the teeth and mucus of fish. As a structural protein, keratin protects animals against interference from the natural environment and other living organisms. Because keratin is rich in disulfide bonds, hydrogen bonds and intermolecular hydrophobic interactions, it is densely structured, stable in nature, insensitive to the action of many chemicals, and difficult to be degraded by common proteases.

Keratinase can specifically degrade insoluble keratin into a soluble protein or polypeptide. Due to its unique specificity for the substrate, keratinase has a good application prospect in the fields of tannery, washing, degradation of keratin waste and feed processing.

The keratinase derived from *Brevibacillus parabrevis* (CGMCC No. 10798) in the invention has poor thermal stability at a relatively high temperature, and the residual enzyme activity is only 38% after incubation at 60° C. for 30 min, which limits the development and promotion of applications of the enzyme in the industrial production. Particularly, during the use in the fields of washing, degradation of keratin waste and feed processing, high-temperature operations are usually involved, which causes deactivation of the enzyme easily. In order to further enhance the application potential of keratinase in industrial production, improvement of the stability of the enzyme to save the cost and improve the utilization efficiency will be an important direction of research on keratinase.

SUMMARY OF THE INVENTION

In order to overcome the above technical problem, invention provides a keratinase mutant, which is produced by mutating at least one of the asparagine at position 181, the tyrosine at position 217, and the serine at position 236 in keratinase derived from *Brevibacillus parabrevis* (CGMCC No. 10798) that is a parent protease In an embodiment of the invention, the asparagine at position 181 is mutated into aspartate.

In an embodiment of the invention, the tyrosine at position 217 is mutated into serine.

In an embodiment of the invention, the serine at position 236 is mutated into cysteine.

In an embodiment of the invention, the parent protease has an amino acid sequence as shown in SEQ ID NO: 4.

In an embodiment of the invention, the mutant has an amino acid sequence as shown in SEQ ID NO: 1, SEQ ID NO: 2 or SEQ ID NO: 13. In another aspect, the invention provides a gene encoding the protease mutant.

In still another aspect, the invention provides a vector carrying the gene.

In an embodiment of the invention, the vector is a pUC vector, a pMD vector, or a pET vector.

In an embodiment of the invention, the vector is vector pET22b(+).

In a further aspect, the invention provides a cell line expressing the keratinase mutant.

In an embodiment of the invention, the host cell can be selected from the group consisting of *Escherichia coli, Bacillus, Corynebacterium*, Yeasts and filamentous fungi.

In another aspect, the invention provides a method for enhancing the thermal stability of keratinase, comprising steps of:

(1) determining a mutation site based on the amino acid sequence of keratinase derived from *Brevibacillus parabrevis* (CGMCC No. 10798);

(2) designing a mutational primer for site-directed mutation of amino acid at the designed mutation site, performing site-directed mutation using a vector carrying the keratinase gene as a template, and constructing a plasmid vector containing the mutant;

(3) transforming the mutant plasmid into a host cell; and (4) selecting a positive clone for fermentation culture and purifying the keratinase mutant.

In an embodiment of the invention, the mutation site is at least one of the asparagine at position 181, the tyrosine at position 217, and the serine at position.

In an embodiment of the invention, the plasmid vector is a pUC vector, a pMD vector, or a pET vector.

In an embodiment of the invention, the host cell for genetic engineering is *Escherichia coli, Bacillus, Corynebacterium*, Yeasts, or filamentous fungi.

In a further aspect, the invention provides a genetically engineered bacteria expressing any of the keratinase mutants of SEQ ID NO: 1-4 in a host cell, where the host cell is *Escherichia coli, Bacillus, Corynebacterium*, Yeasts, or filamentous fungi.

In another aspect, the invention also provides use of the keratinase mutant in the fields of biology, food or chemical engineering.

In an embodiment of the invention, the keratinase mutant is used in the treatment of waste keratin resources, leather dehairing, feed processing, and other areas.

By means of the above technical solutions, the invention has the following advantages as compared with the prior art: The invention achieves the improvement of the thermal stability of the keratinase mutant under the same conditions. Compared with the wild-type enzyme, the half-lives of the Y217S, S236C and N181D mutant enzymes at 60° C. are extended by 3.05 times, 1.18 times and 1 time, respectively, and T50 is also increased by 5.4° C., 2.8° C. and 2° C., respectively. The specific enzyme activities of double-point mutant N181D-Y217S and N181D-S236C are increased by 58% and 15%, respectively, T50 is increased by 5.1 and 2.9° C., respectively, and the half-life at 60° C. is 4.09 times and 1.54 times that of WT, respectively; and the optimum reaction temperature is increased by 10° C. and 5° C., respectively. Therefore, the keratinase mutant has a better application prospect in industrial production than the parent keratinase.

DETAILED DESCRIPTION OF THE PREFERRED EMBODIMENTS

Figure 1:
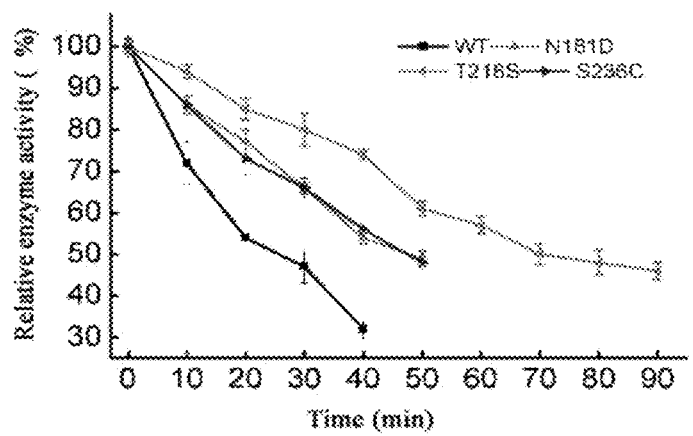
FIG. 1 shows the inactivation curves of the wild-type enzyme and mutant enzymes at 60° C.

The invention will be further illustrated in more detail with reference to the accompanying drawings and embodiments. It is noted that, the following embodiments only are intended for purposes of illustration, but are not intended to limit the scope of the present invention.

Keratinase activity assay method: The enzyme activity is determined by UV colorimetry using 1% keratin as a substrate. 1.5 mL of the substrate is added to 0.5 mL of appropriately diluted enzyme solution, and incubated at 40° C. for 15 min. Then, 2 mL of 0.4 M TCA solution is added, allowed to stand for 10 min and then centrifuged at 12000 r·min$^{-1}$ for 5 min. 500 μL of the supernatant is taken out, 2500 μL of 0.4 M Na2CO3 and 500 μL of Folin-Ciocalteu reagent are added, mixed uniformly, incubated and reacted at 40° C. for 20 min, and developed. Then, OD$_{660}$ is detected.

Definition of enzyme activity: In the above reaction system, every 0.01 increase in the absorbance at 660 nm is defined as 1 enzyme unit (U·mL$^{-1}$).

Determination of half-life of keratinase: An appropriate amount of the parent keratinase and each mutant enzyme solutions are incubated at 60° C., and the residual enzyme activity is determined by sampling at an interval of 10 min. Time is indicated on the x-axis, the fitted relative enzyme activity is indicated on the y-axis, and the half-life ($t_{1/2, 60° C.}$) of the enzyme at 60° C. is calculated according to the formula t=ln 2/k.

Determination of T$_{50}$ of keratinase: The parent keratinase and mutant enzyme solutions are incubated at various temperatures (40-65° C.). Samples are taken periodically and cooled immediately in an ice bath, and the residual enzyme activity is determined. The activity of the parent keratinase cooled for the same time in the ice bath is defined as 100%.

Embodiment 1

Preparation of Site-Directed Single Keratinase Mutant

According to the amino acid sequence (as shown in SEQ ID NO: 4) of keratinase derived from *Brevibacillus parabrevis* (CGMCC No. 10798), primers introducing Y217S, N181D and S236C mutations were designed respectively. The asparagine (Asn) at position 181 of the parent keratinase (WT) was mutated into aspartate (Asp), to give an amino acid sequence as shown in SEQ ID NO: 1. The tyrosine (Tyr) at position 217 was mutated into serine, to give an amino acid sequence as shown in SEQ ID NO: 2. The serine (Ser) at position 236 was mutated into cysteine (Cys), to give an amino acid sequence as shown in SEQ ID NO: 3. The keratinase gene was subjected to site-directed mutations, and the DNA coding sequences were determined. The mutant genes were transferred to an expression vector and introduced into the expression host *E. coli* for expression, to obtain single-point keratinase mutants Y217S, N181D and S236C. In the PCR reaction, the vector pET22b-bpker was used as a template.

The primer for introducing N181D site-directed mutation is:

```
N181D-F:
                                        (SEQ ID NO: 5)
5'-TTGCCAATGTA(GAT)AGTAACAA-3'

(the parenthesized are mutation bases)

N181D-R:
                                        (SEQ ID NO: 6)
5'-TGACATTGTTACT(ATC)TACATTGG-3'

(the parenthesized are mutation bases)
```

The primer for introducing Y217S site-directed mutation is:

```
Y217S-F:
                                        (SEQ ID NO: 7)
5'-GGATACACTTCTTAT(AGC)GGAACA-3'

(the parenthesized are mutation bases)

Y217S-F:
                                        (SEQ ID NO: 8)
5'-CCATAGATGTTCC(GCT)ATAAGAAG-3'

(the parenthesized are mutation bases)
```

The primer for introducing S236C site-directed mutation is:

```
S236C-F:
                                        (SEQ ID NO: 9)
5'-CAGCGCTTATTCTT(TGC)AAAACC-3'

(the parenthesized are mutation bases)

S236C-R:
                                        (SEQ ID NO: 10)
5'-TTCGGGTTTTT(GCA)AAGAATAAG-3'

(the parenthesized are mutation bases)
```

The PCR amplification procedure was set to: pre-denaturation at 95° C. for 6 min; then 30 cycles of denaturation at 95° C. for 10 s, annealing for 5 s, and extension at 72° C. for 6 min and 30 s; and extension at 72° C. for 60 min, and incubation at 4° C. The PCR product was detected by 1% agarose gel electrophoresis.

The PCR product was treated with Dpn I endonuclease at 37° C. for 2-3 hrs to digest the methylated template plasmid, and then transformed into E. coli JM109. The clone was picked, inoculated into an LB liquid medium (containing 100 μg/mL Amp) and incubated for about 10 h. The plasmid was extracted, and the mutated plasmid sequenced correctly was transformed into E. coli BL21(DE3) competent cells to obtain a recombinant strain expressing the mutant.

Embodiment 2

Preparation of Site-Directed Double Keratinase Mutant

The tyrosine (Tyr) at position 217 of the single mutant enzyme Y217S was mutated into serine, or the serine (Ser) at position 236 of the single mutant enzyme N181D was mutated into cysteine (Cys), which was designated as N181D-Y217S or N181D-S236C respectively. The mutant genes were transferred to an appropriate expression vector and introduced into the expression host E. coli for expression, to obtain a single mutant keratinase, and obtain a double mutant keratinase.

Site-directed mutation of double mutants N181D-Y217S, N181D-S236C: Rapid PCR technique was used, and the expression vectors pET22b(+)-Y217S, and pET22b(+)-S236C were used as templates.

The primer of site-directed mutation for introducing N181D mutation is:

```
N181D-F:
                                   (SEQ ID NO: 11)
5'-TTGCCAATGTA(GAT)AGTAACAA-3'

(the parenthesized are mutation bases)

N181D-R:
                                   (SEQ ID NO: 12)
5'-TGACATTGTTACT(ATC)TACATTGG-3'

(the parenthesized are mutation bases)
```

The primer for introducing S236C site-directed mutation is:

```
S236C-F:
                                   (SEQ ID NO: 13)
5'-CAGCGCTTATTCTT(TGC)AAAAACC-3'

(the parenthesized are mutation bases)

S236C-R:
                                   (SEQ ID NO: 14)
5'-TTCGGGTTTTT(GCA)AAGAATAAG-3'

(the parenthesized are mutation bases)
```

The PCR reaction conditions and the sequencing methods of mutant genes were as described for single mutants.

(3) Enzyme Production by Fermentation and Enzyme Purification

The recombinant keratinase expressing host strain was induced to express, and centrifuged at 12000 r min$^{-1}$ and 4° C. to collect the supernatant of the fermentation broth. The protein in the fermentation broth was concentrated by ammonium sulfate of 70% saturation, and the supernatant was removed by high-speed low-temperature centrifugation. Then, the obtained pellet was redissolved in an appropriate amount of buffer, and then the pellet was removed by high-speed low-temperature centrifugation, followed by filtration through a 0.22 μm microporous filter to remove the impurities. The recombinant keratinase with His-tag was purified by IKTA Purifier using a nickel ion affinity column (HisTrap FF).

Embodiment 3

Effect of pH on enzyme activity: 1% keratin substrate was prepared with buffer systems of pH 6-12, and the enzyme solution was diluted by appropriate times with different buffer systems. Then the activity of keratinase was determined at 40° C., to determine the optimum pH for reaction. Determination of stability of keratinase against pH: The keratinase was appropriately diluted with buffers of different pH values and incubated for 1.0 hr at room temperature, and then the residual enzyme activity was determined under a reaction condition of 40° C. The various buffer systems included citrate buffer (pH 5.0-6.0), Tris-HCl buffer (pH 7.0-9.0), glycine-NaOH buffer (pH 10.0) and KCl—NaOH (pH 11.0-12.0).

Effect of temperature on enzyme activity: An appropriate amount of keratinase was taken to determine enzyme activity at 30-70° C. The temperature corresponding to the highest enzyme activity was the optimum temperature. Conditions for determination of stability of recombinant keratinase against temperature: The enzyme was treated at various temperatures for 30 min, and then the residual enzyme activity was determined.

Figure 2:
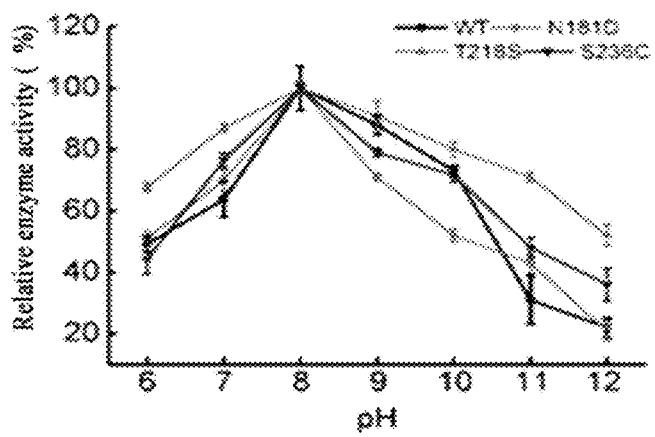
FIG. 2 shows the optimum temperature for the wild-type enzyme and single-point mutant enzymes.
Figure 3:
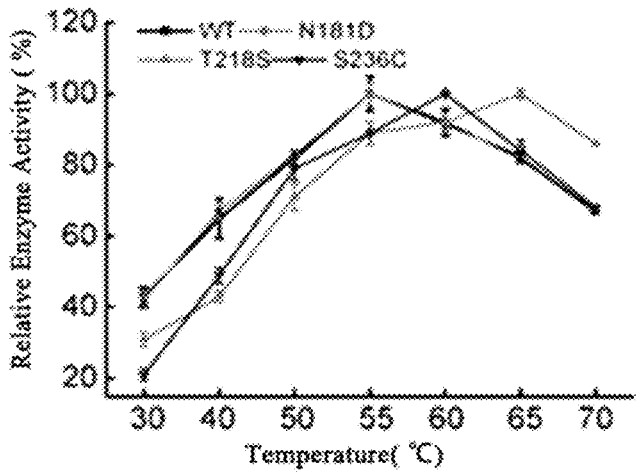
FIG. 3 shows the optimum pH for the wild-type enzyme and single-point mutant enzymes.

As compared with WT, the stability of the mutants N181D, Y217S and S236C is significantly improved. Y217S has the highest increase, the half-life at 60° C. is extended by 3.05 times, and $T_{50}$ is increased by 5.4° C. $t_{(1/2,\ 60°\ C.)}$ of the mutants N181D and S236C is twice that of WT, and $T_{50}$ is also 2° C. and 2.8° C. higher than that of WT (Table 1 and FIG. 1). The optimum pH for reaction of the mutants Y217S and S236C is the same as that of WT (FIG. 2). Among these enzymes, Y217S and S236C have an optimum temperature for reaction that is respectively 10° C. and 5° C. higher than that of WT (FIG. 3).

TABLE 1

Stability parameters of wild enzyme and mutant enzymes

| Strain | $t_{(1/2,\ 60°\ C.)}$(min) | $T_{50}$(° C.) |
|---|---|---|
| WT | 22 ± 0.3 | 57.3 |
| N181D | 46 ± 0.2 | 59.3 |
| Y217S | 89 ± 0.2 | 62.7 |
| S236C | 48 ± 0.6 | 60.1 |

The effect of combined mutations on the characteristics of the enzymes is shown in Table 2. Compared with WT, N181D-Y217S has a specific enzyme activity that is increased by 58%; a $T_{50}$ that is increased by 5.1° C.; an optimum temperature for reaction that is increased by 10° C.; and also an obviously extended half-life at 60° C. that is 4.09 times that of WT. The optimum pH for reaction of the enzyme with combined mutations is 8.0.

TABLE 2

Catalytic performance of enzymes with combined mutations

| Enzyme | Specific enzyme activity (U · mg$^{-1}$) | Optimum temperature (° C.) | Optimum pH | $t_{(1/2,\ 60°\ C.)}$ (min) | $T_{50}$(° C.) |
| --- | --- | --- | --- | --- | --- |
| WT | 6005 ± 89 | 55 | 8.0 | 22 ± 0.3 | 57.3 |
| N181D-Y217S | 9504 ± 105 | 65 | 8.0 | 90 ± 0.5 | 62.4 |
| N181D-S236C | 6888 ± 57 | 60 | 8.0 | 34 ± 0.5 | 57.9 |

Embodiment 4

N181D, Y217S, and N181D-Y217S mutant enzymes all have a $K_m$ that is lower than that of WT, and a Kcat/$K_m$ that is higher than that of WT, in which the $K_{cat}/K_m$ of Y217S is 37% higher than that of WT. On the contrary, S236C has a $K_m$ that is higher than that of WT, but the $K_{cat}/K_m$ is slightly lower. This indicates that the affinity and catalytic efficiency for the substrate of N181D, Y217S and N181D-Y217S mutant enzymes are higher than those of WT, and the catalytic performance of the enzyme is improved.

TABLE 3

Kinetic parameters of wild-type and mutant enzymes

| Enzyme | $K_m$ (mM) | $K_{cat}$ (s$^{-1}$) | $K_{cat}/K_m$ (s$^{-1}$ · mM$^{-1}$) |
| --- | --- | --- | --- |
| WT | 2.1 ± 0.12 | 26.3 ± 2.01 | 12.5 |
| N181D | 1.9 ± 0.29 | 28.7 ± 1.52 | 15.1 |
| Y217S | 1.5 ± 0.21 | 31.3 ± 3.11 | 20.7 |
| S236C | 2.2 ± 0.18 | 25.9 ± 1.83 | 11.7 |
| N181D-Y217S | 1.8 ± 0.22 | 27.6 ± 2.11 | 15.3 |

Embodiment 5

Three-Dimensional Structure Analysis of Wild-Type and Mutant Enzymes

1. Flexibility Analysis

Figure 4:
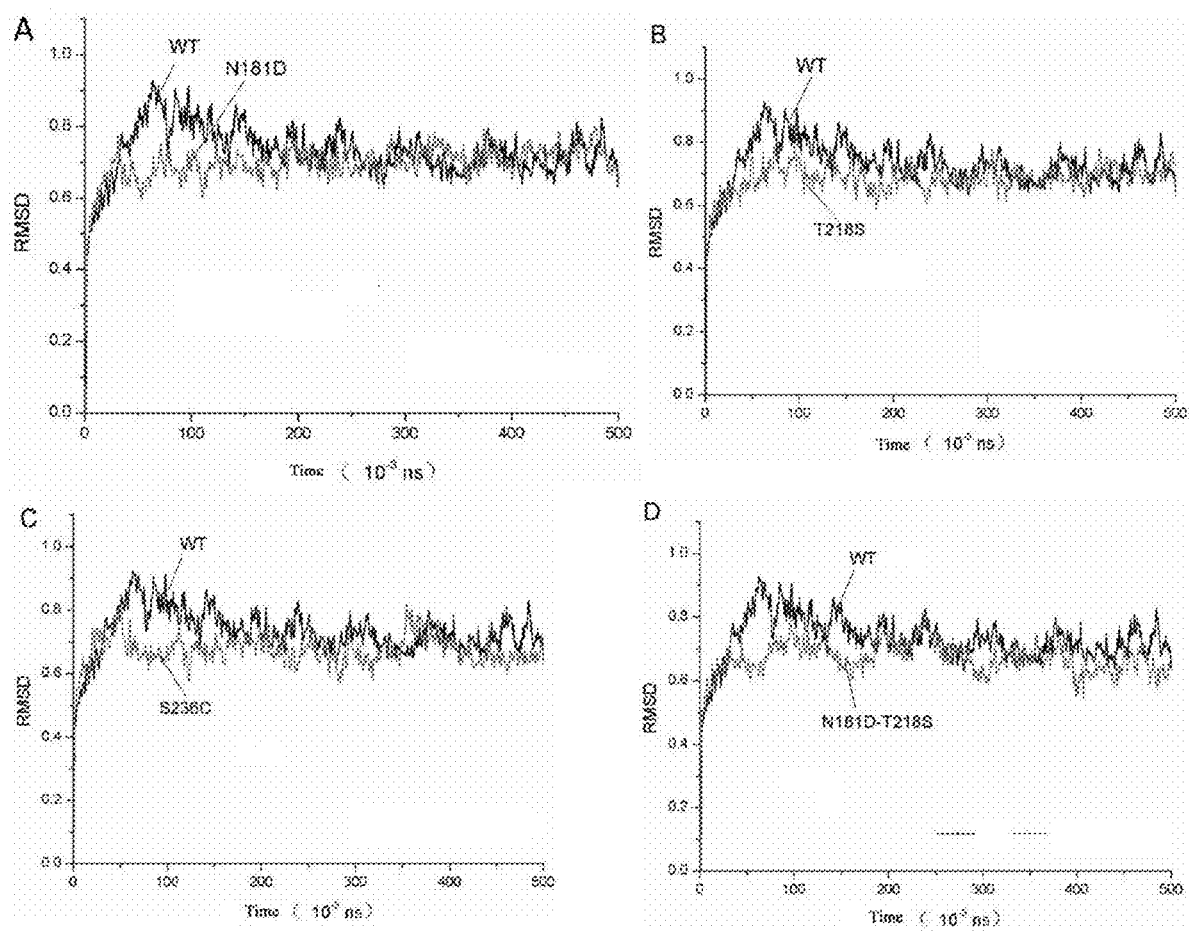
FIG. 4 shows corresponding RMSD curves of the wild-type enzyme and mutant enzymes.

The RMSD value is the statistical deviation of the structural conformation of all atoms from the target conformation at each moment during a high-temperature simulation process in molecular dynamics. It reflects the overall structural flexibility at high temperature and is an important parameter to measure the stability of the protein system. It can be seen from FIG. 4 that after the molecular dynamics simulation reaches equilibrium, the average RMSD of WT is higher than that of Y217S, S236C and Y217S-S236C mutant enzymes. Therefore, mutations at these sites reduce the flexibility of the overall conformation of keratinase, and thus the enzyme is more stable at high temperature.

2. Structure Analysis (1) Hydrogen Bonds Forming

The number of hydrogen bonds between the amino acids in a globular region with a radius of 5 Å centered at the mutation site and in the surrounding amino acids of the wild-type and mutant enzymes was calculated by molecular dynamics simulation (Table 4).

TABLE 4

Hydrogen bonds formed in local regions of wild and mutant enzymes

| Mutation site | WT | Mutant enzyme |
| --- | --- | --- |
| N181D | 10 | 13 |
| Y217S | 10 | 11 |
| S236C | 20 | 23* |
| N181D-Y217S | 17 | 21 |

Note:
*a salt bridge is formed.

Figure 5:
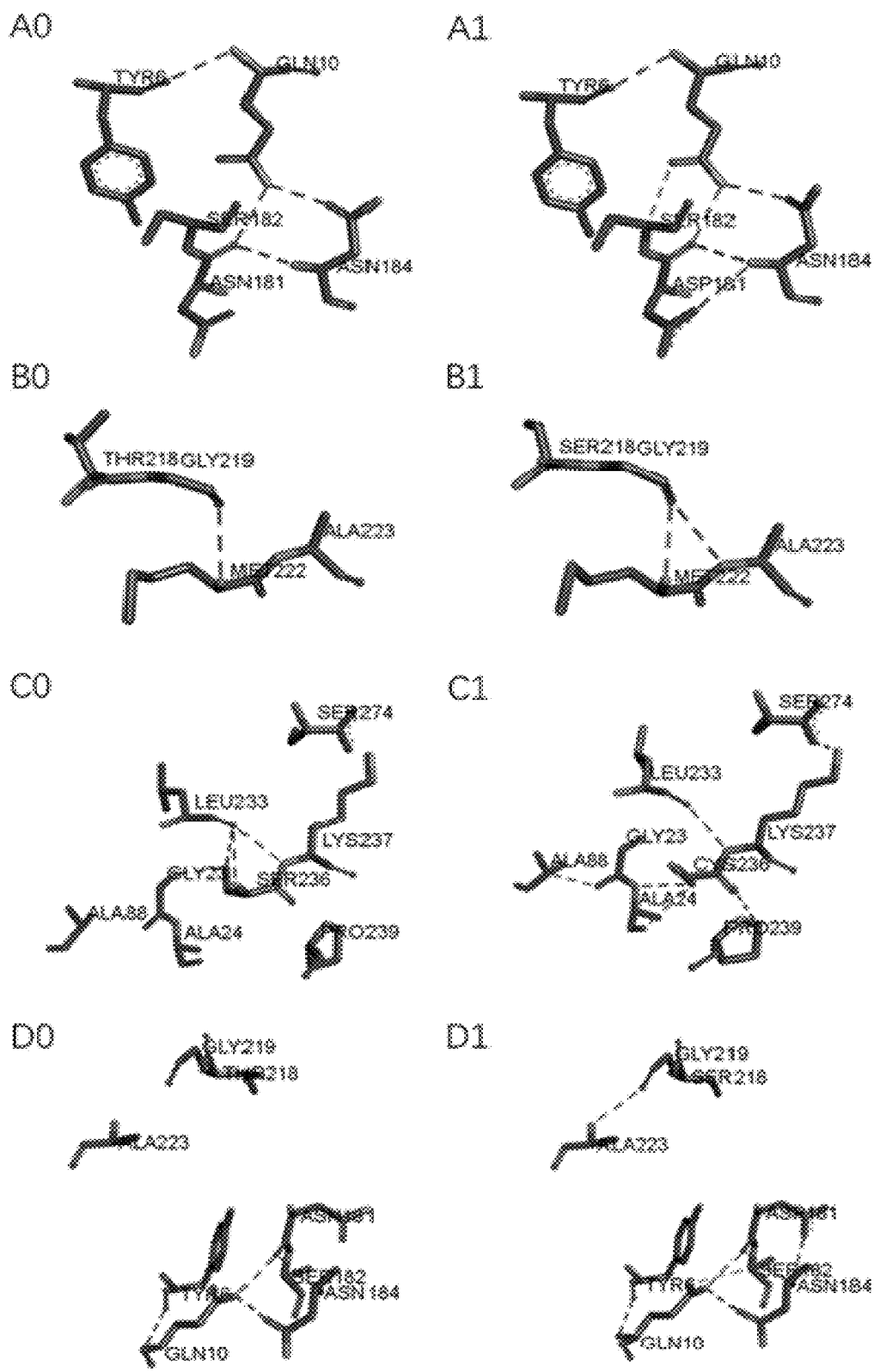
FIG. 5 shows the comparison of the hydrogen bonds in the vicinity of the mutation sites of WT and mutants N181D, Y217S, S236C, and N181D-Y217S. A0: in the vicinity of position 181 of WT; A1: in the vicinity of position 181 of N181D; B0: in the vicinity of position 217 of WT; B1: in the vicinity of position 217 of Y217S; C0: in the vicinity of position 236 of WT; C1: in the vicinity of position 236 of S236C; D0: in the vicinity of positions 181 and 217 of WT; and D1: in the vicinity of positions 181 and 217 of N181D-Y217S.

It can be seen from the calculation by molecular dynamics simulation of the mutants (FIG. 5) that compared with WT, the N181D mutant enzyme has two hydrogen bonds formed in the vicinity of the mutation site, that is, Asn184(N)-Asp181(OD1) and Ser182(CA)-Gln10(OE1). Compared with WT, the 217-Tyr in the 213-218 (3-sheet structure of the Y217S mutant enzyme is replaced by Ser, which promotes the formation of a hydrogen bond between Gly-219 at the turn and Ala-223 located in an a helix of 220Thr-237Lys, thus allowing the sheet to be more closer to the helix and enhancing the rigid structure of the protein. In the mutant S236C, the terminal amino group of Lys-237 and the carboxyl group of Ser-274 are close to each other to form a salt bridge Lys237(NZ)-Ser274(OXT). Further, in the S236C mutant, a hydrogen bond is formed between Ala-88 and Gly-23, and between Pro-239 and Cys-236 respectively (Ala88 (CA)-Gly23(O), Pro239(CD)-Cys236(O)), which makes great contributions to the thermal stability of the structure of the protein.

Thermal stability is of great significance for the study of enzymes. In the process of protein folding, adjacent sites carry opposite charges, which can contribute to the formation of traditional hydrogen bonds and salt bridges; and the traditional hydrogen bonds and salt bridges are closely related to the structure and function of proteins. The increase in thermal stability promotes the applications of the enzyme mainly by improving the operational stability of the enzyme, prolonging the service cycle of the enzyme, reducing the amount of the enzyme used and reducing the cost, and by the ability to withstand higher-temperature operation conditions.

(2) Surface Charge of Protein

Figure 6:
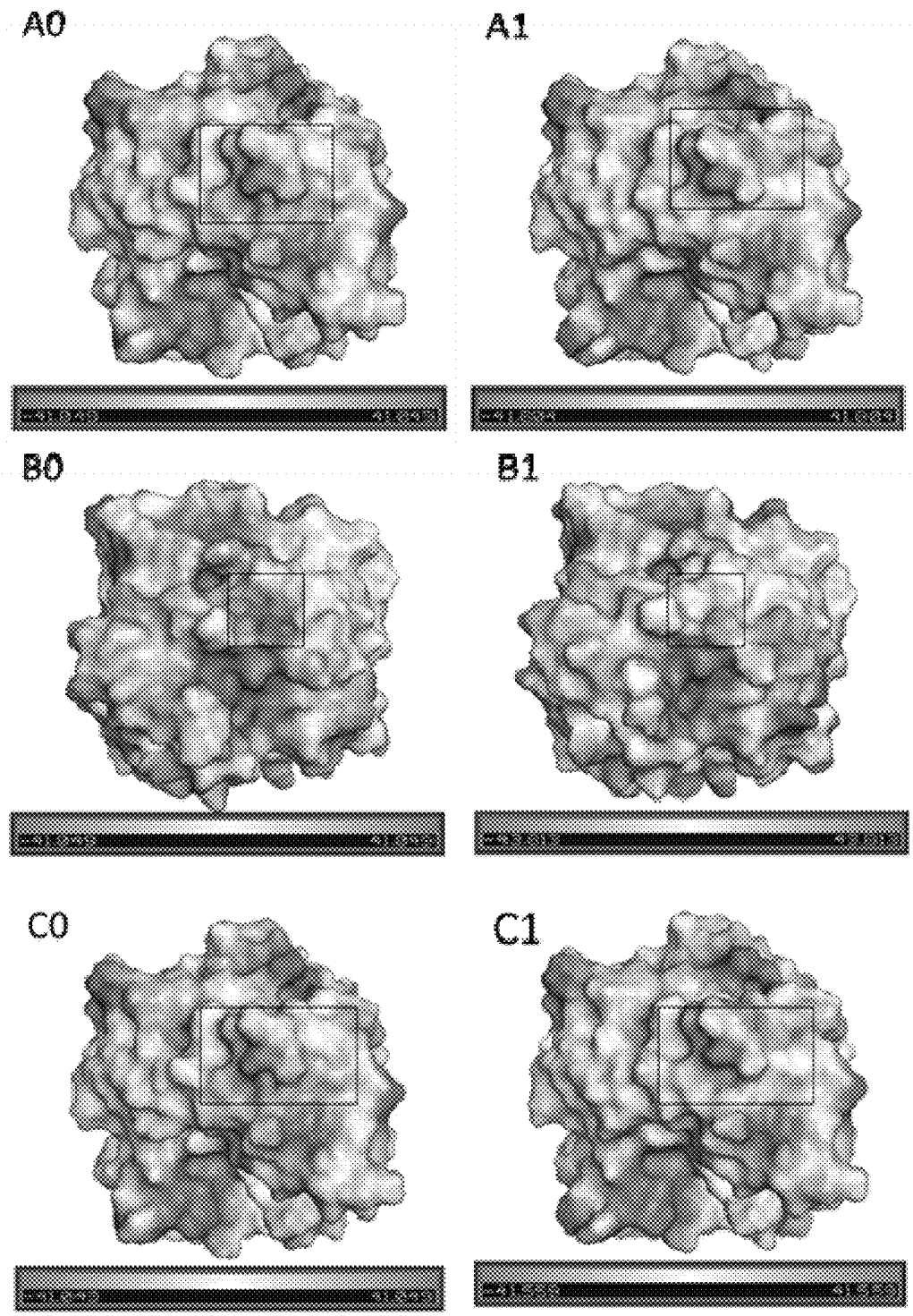
FIG. 6 shows the comparison of the surface charge of the amino acids at positions 181, 236, and 181-217 of WT and mutants N181D, S236C, and N181D-Y217S. Left side: A0, B0, and C0, WT; right side: A1, N181D; B1, S236C; C1, N181D-Y217S.

The surface charge on the spatial structure of WT and mutant enzyme proteins is shown in FIG. 6. Compared with WT, the surface charge of N181D, S236C and N181D-Y217S proteins is significantly reduced. Except these regions, the surface charge distributions of WT and mutant enzymes in other regions are more consistent. This indicates that the mutants have less surface charges and a more compact structure, thus, the protein conformation is more stable at high temperatures.

The above description is only preferred embodiments of the present invention and not intended to limit the present

What is claimed is:

1. A keratinase mutant, which is obtained by creating amino acid mutation(s) in the parent keratinase amino acid sequence comprising SEQ ID NO: 4 which is derived from *Brevibacillus parabrevis* (CGMCC 10798), wherein at least one of the asparagine at position 181, the tyrosine at position 217 and the serine at position 236 are mutated.

2. The keratinase mutant according to claim 1, wherein the asparagine at position 181 is mutated into aspartate.

3. The keratinase mutant according to claim 1, wherein the tyrosine at position 217 is mutated into serine.

4. The keratinase mutant according to claim 1, wherein the serine at position 236 is mutated into cysteine.

5. A method for producing a mutant according to claim 1, comprising steps of:

(1) determining a mutation site based on the amino acid sequence of the parent keratinase, designing a primer for site-directed mutation, performing site-directed mutation using a vector or template carrying the keratinase-coding gene, and constructing a vector containing the mutant;
(2) transforming the vector containing the mutant-coding gene into a host cell; and
(3) selecting a positive clone for fermentation-induced culture and purifying the keratinase mutant.

6. The method according to claim 5, wherein the vector is selected from the group consisting of a pUC vector, a pMD vector, and a pET vector.

7. The method according to claim 5, wherein the host cell for genetic engineering is selected from the group consisting of *Escherichia coli, Bacillus, Corynebacterium*, Yeasts, and filamentous fungi.

8. The method according to claim 5, wherein the mutation site is at least one of the asparagine at position 181, the tyrosine at position 217, and the serine at position 236.

9. A gene encoding the keratinase mutant according to claim 1.

10. A vector carrying the gene according to claim 9.

11. The vector according to claim 10, wherein the vector is a pUC vector, a pMD vector or a pET vector.

12. A cell line expressing the keratinase mutant according to claim 1.

13. A genetically engineered host cell, expressing the keratinase mutant according to claim 1, wherein the host cell is *Escherichia coli, Bacillus, Corynebacterium*, Yeasts, and filamentous fungi.

* * * * *